(12) United States Patent
Kleinschmitt (10) Patent No.: US 7,206,667 B2
(45) Date of Patent: Apr. 17, 2007

(54) ROBOT ALIGNMENT SYSTEM AND METHOD

(75) Inventor: David Kleinschmitt, Bethel, CT (US)

(73) Assignee: Siemens Medical Solutions Diagnostics, Tarrytown, NY (US)

( * ) Notice: Subject to any disclaimer, the term of this patent is extended or adjusted under 35 U.S.C. 154(b) by 340 days.

(21) Appl. No.: 10/871,463

(22) Filed: Jun. 18, 2004

(65) Prior Publication Data

US 2005/0283274 A1    Dec. 22, 2005

(51) Int. Cl.
G06F 19/00 (2006.01)
(52) U.S. Cl. .............. 700/245; 700/254; 700/249; 700/250; 700/258; 700/259; 700/260; 700/261; 700/262; 700/264; 901/49; 414/744.5; 74/490.03
(58) Field of Classification Search ............... 700/245, 700/254
See application file for complete search history.

(56) References Cited

U.S. PATENT DOCUMENTS

| | | | |
|---|---|---|---|
| 4,368,913 A * | 1/1983 | Brockmann et al. ........ 294/106 |
| 5,108,703 A * | 4/1992 | Pfost et al. ................... 422/65 |
| 5,125,748 A * | 6/1992 | Bjornson et al. ........... 356/414 |
| 5,128,103 A * | 7/1992 | Wang et al. .................. 422/64 |
| 5,158,895 A * | 10/1992 | Ashihara et al. ............ 436/526 |
| 5,166,889 A * | 11/1992 | Cloyd .......................... 702/22 |
| 5,294,404 A * | 3/1994 | Grandone et al. ............ 422/64 |
| 5,415,840 A * | 5/1995 | Sano et al. ................... 422/67 |
| 5,482,863 A * | 1/1996 | Knobel ......................... 436/54 |
| 5,769,775 A * | 6/1998 | Quinlan et al. .............. 494/10 |
| 2005/0080512 A1* | 4/2005 | Critchlow ................... 700/245 |

\* cited by examiner

*Primary Examiner*—Thomas Black
*Assistant Examiner*—McDieunel Marc
(74) *Attorney, Agent, or Firm*—Rodman & Rodman (57) ABSTRACT

The robot alignment system is used for establishing a predetermined alignment position between a movable robot member and an article that is processed by the robot. The system includes a laser transmitter that emits a focused laser beam and a target against which the focused laser beam is directed. The laser transmitter is preferably supported by the robot and the target is supported by the article that is processed by the robot. A signaling device cooperates with the target to produce a detectable signal when the focused laser beam is received at a predetermined location on the target. The detectable signal signifies establishment of a predetermined alignment position between the robot and the article that is processed by the robot.

21 Claims, 7 Drawing Sheets

ROBOT ALIGNMENT SYSTEM AND METHOD

BACKGROUND OF THE INVENTION

This invention is directed to a system and method for establishing alignment of an automated movable operating member with an article that is processed by the movable operating member, and more particularly to a robot alignment system and method for aligning a robot operating member with an article that is automatically processed by the robot.

Robots have long been used to perform processing operations that were previously performed manually, such as painting, polishing, soldering, assembling, machining and mixing, to name a few. A robot can include one or more manipulative members such as robot arms, which are generally referred to herein as robot operating members. Robots are also used to transport articles from one location to another and/or perform processing operations other than those previously indicated.

The term "processing" as used herein is intended to refer to any type of operation performed by a robot on or with an article. Also, the term "robot" may be used interchangeably herein with the term "robot operating member."

U.S. Pat. No. 6,293,750 shows a blood sample analysis system that incorporates at least one robot to retrieve and transport containers such as sample tubes from one location to another for a variety of processing operations. The robot is movably supported on an overhead horizontal beam for back and forth movement, rotational movement about a vertical axis, and up and down movement along the vertical axis.

In other known robot systems a robot can be movably supported on a platform or base, for performing a predetermined operation. Generally, in most currently used robot systems, whether the robot is supported overhead or on a platform or base, the movement of the robot is usually automatically controlled by a programmable computerized control system.

Thus, using known programming techniques, a robot control system can be programmed to provide automated movement of the robot to one or more selected locations in a predetermined sequence to perform one or more processing operations. For example, in the robot system of U.S. Pat. No. 6,293,750 the robot moves automatically to a first location to pick up a sample tube, transports the sample tube to a second location, releases the sample tube at the second location and returns to the first location to repeat the pickup and delivery operation.

Programming of the movement and function of a robot, such as the robot of U.S. Pat. No. 6,293,750, to move to one or more selected locations to perform a pick up and/or delivery operation often requires that a precise alignment position be established between the robot and the article that is processed by the robot. Thus the robot must be precisely aligned with the article that is to be processed before the robot can begin to perform the processing operation. The robot must also be precisely aligned with a desired delivery location before the robot releases the article at the delivery location.

Therefore, during programming of a robot control system, the precise location of a pickup and delivery position for example, and any other necessary positional information is communicated to the robot control system so that the control system can accurately govern repetitive automated movement of the robot to selected pick-up and delivery positions.

For example, once a sample tube pick-up position and a sample tube delivery or drop-off position are established and communicated to the robot control system, the control system can be programmed to automatically move the robot to the selected pick-up and delivery positions to perform the desired processing operations.

In some instances the robot and the article being processed are each separately moved to an alignment position. In other instances the article that will be processed by the robot does not move independently of the robot. The robot thus moves to an alignment position with the article, before the article is processed by the robot. The actual processing operation is also usually controlled by the robot control system.

One known method of establishing alignment between a robot and an article that is processed by the robot includes providing the robot with a first alignment pin (the robot pin) and providing the article being processed with a second alignment pin (the article pin). The robot pin and the article pin generally have the same directional orientation such as vertical, horizontal, or inclined, for example. The robot is moved, in any suitable known manner, to a selected alignment position wherein the robot pin aligns with the article pin. Alignment is usually established when a programming operator makes a visual determination that the robot pin and the article pin are in alignment.

The programming operator then communicates the alignment position to the robot control system, in any suitable known manner, to thereby program the alignment information in the robot control system. The robot control system is thus programmed to automatically move the robot to the selected alignment position to begin processing of the article. Other alignment positions can be programmed in similar fashion in the robot control system to govern further movement and functional operations of the robot on articles being processed by the robot.

During programming of alignment positions in a robot control system, it has been found that visual recognition of alignment between a robot pin and an article pin can be inaccurate. Such inaccuracy can occur because of depth perception problems of an operator, as well as other problems of visual acuity that an operator may have. Visual problems of an operator as well as human error in establishing an alignment position are further compounded when space limitation problems prevent an operator from being close enough to a robot system to clearly discern when there is alignment between the robot pin and the article pin.

It is thus desirable to provide an alignment system and method for establishing a predetermined alignment position between a movable operating member and an article processed by the operating member, wherein the alignment system does not rely on visual acuity of a programming operator.

OBJECTS AND SUMMARY OF THE INVENTION

Among the several objects of the invention may be noted the provision of a novel alignment system for establishing a predetermined alignment position between a movable operating member and an article that is processed by the movable operating member, a novel alignment system that uses a laser beam and a laser responsive signaling device for aligning an operating member and an article that is processed by the operating member, a novel alignment system that generates a detectable signal when alignment is established between an operating member and an article that is processed by the operating member, a novel robot alignment system including a laser transmitter carried by a robot member and a laser responsive signaling device carried by the article that is processed by the robot member, or vice-versa, a novel alignment system having a laser responsive signaling device that produces a detectable signal when alignment is established between an operating member and an article that is processed by the operating member, a novel method of establishing a predetermined alignment position between an operating member and an article that is processed by the operating member and a novel method of establishing a predetermined alignment position between a robot member and an article that is processed by the robot member.

The invention accordingly comprises the constructions and methods hereinafter described, the scope of the invention being indicated in the claims.

DESCRIPTION OF THE DRAWINGS

In the drawings.

Corresponding reference numbers indicate corresponding parts throughout the several views of the drawings.

DETAILED DESCRIPTION OF THE INVENTION

Figure 1:
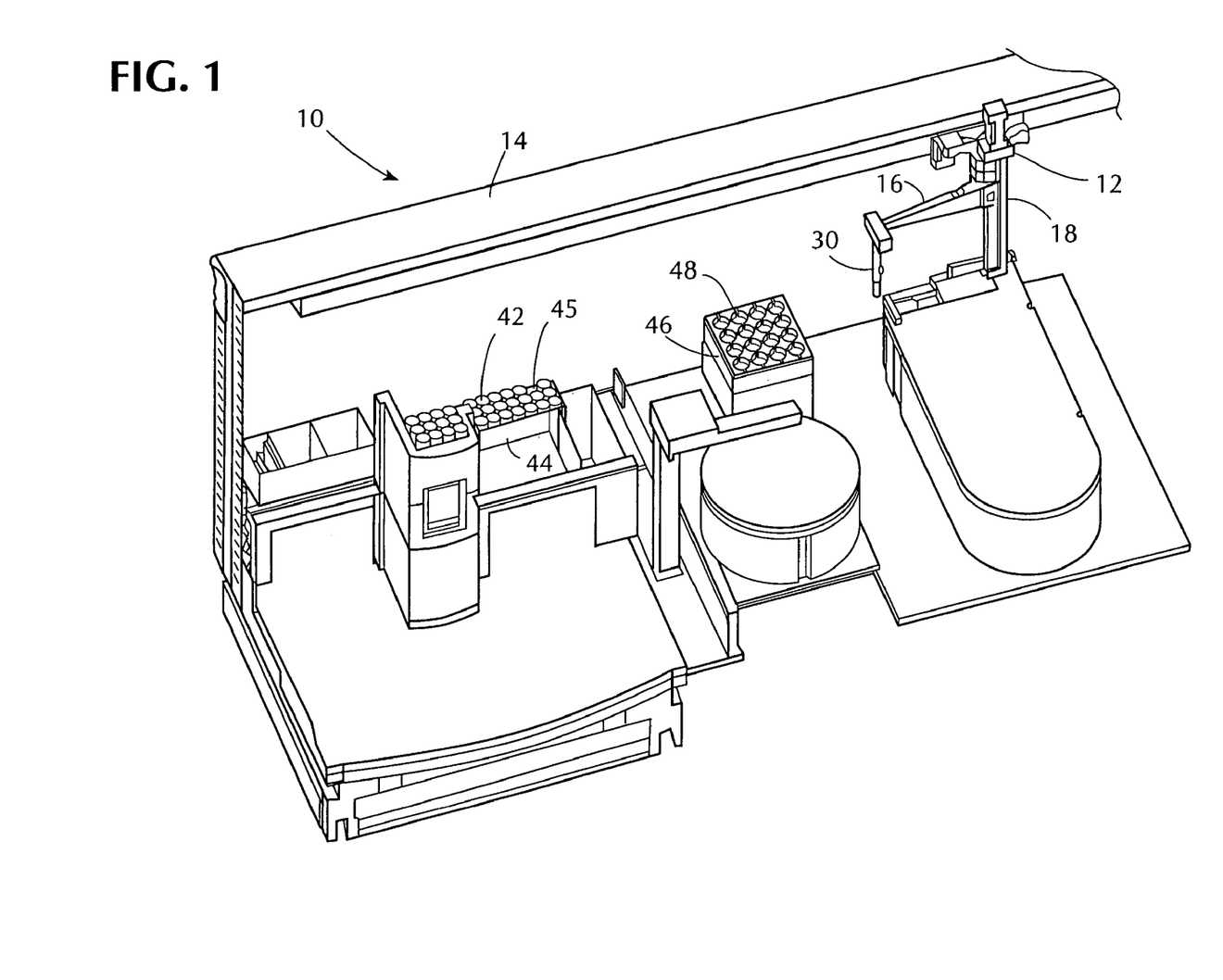
FIG. 1 is a simplified schematic perspective view of a sample analysis system with a robot having a gripper member.

Referring to the drawings, FIG. 1 shows a sample analysis system 10 that includes a robot 12 supported on a rail 14 for back and forth movement in a horizontal direction, as described in detail in U.S. Pat. No. 6,293,750, the disclosure of which is incorporated by reference herein.

Figure 2:
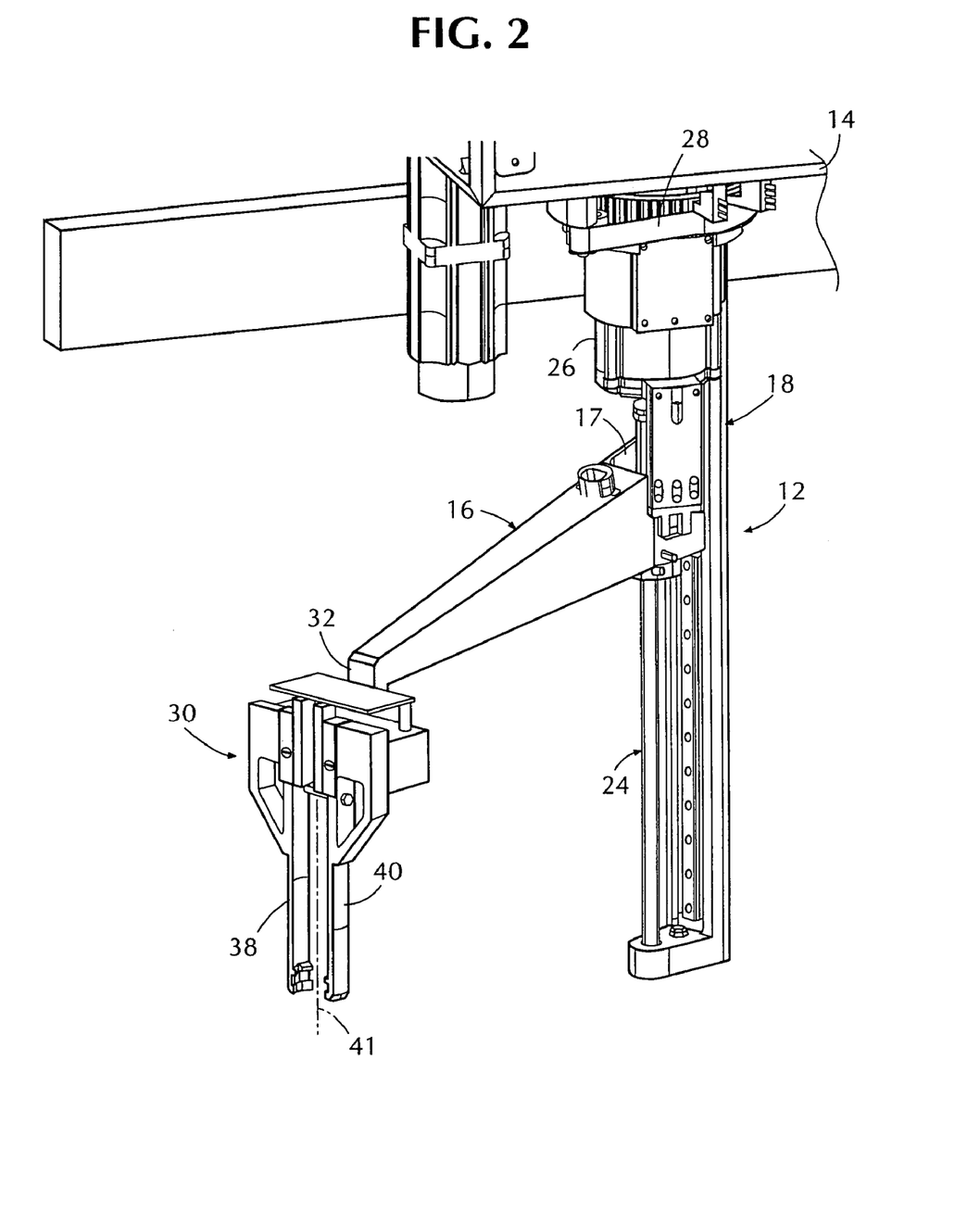
FIG. 2 is an enlarged perspective view of the robot.

The robot 12 (FIG. 1) includes a generally horizontal robot arm 16 having an inner end 17 (FIG. 2) joined to a vertical member 18. The vertical member 18 of the robot 12 includes a rotatable vertical screw assembly 24 (FIG. 2) operable by a motor 26 for raising and lowering the robot arm 16 in a vertical direction. A second motor (not shown) provided proximate an upper end 28 (FIG. 2) of the vertical member 18 is operable to swing the robot arm 16 about a vertical axis that corresponds to the vertical member 18.

A robot gripper member 30 (FIG. 2) is attached to an outer end 32 of the robot arm 16 and includes spaced and parallel gripper fingers 38 and 40. The gripper fingers 38 and 40 are movable in parallel relationship toward and away from a gripper finger axis 41 (FIG. 3) midway between the gripper fingers 38 and 40. The gripper fingers 38 and 40 can grip an article such as a cylindrical sample tube 42 (FIG. 1), located in a first sample tube rack 44. The first sample tube rack 44 has a plurality of sample tube containment openings or sample tube containment positions 45 (FIG. 1), each of which can be occupied by a respective sample tube 42.

The robot 12 is used for automatic processing of articles, including automatic transfer of sample tubes 42 (FIG. 1) from the first sample tube rack 44 to a second sample tube rack 46 within the sample analysis system 10. Other articles, including reagent containers (not shown) can also be automatically processed by the robot 12 in the sample analysis system 10.

In order to process the sample tubes 42 the robot 12 must be programmed to move to the first sample tube rack 44 (FIG. 1) and automatically stop at a predetermined sample tube containment position 45 such that the robot gripper member 30 aligns with a selected sample tube 42 in the predetermined sample tube containment position 45.

The robot gripper finger axis 41 (FIGS. 2 and 3), must therefore align with an individual selected sample tube 42 of the first sample tube rack 44. Such alignment is also referred to as a robot alignment position. When the robot 12 is in a robot alignment position the gripper fingers 38 and 40 can accurately grip and remove the selected sample tube 42 from the first sample tube rack 44 for transport to and release in a selected sample tube containment position 48 (FIG. 1) in the second sample tube rack 46.

Once a robot alignment position of the robot gripper fingers 38 and 40 with a sample tube 42 is initially determined, the robot control system (not shown) is programmed to automatically move the robot 12 to the robot alignment position. A programming of robot alignment positions for each sample tube containment position 45 in the first sample tube rack 44 enables the robot 12 to repeatedly and automatically carry out desired transfers of sample tubes 42 from the first sample tube rack 44 to the second sample tube rack 46.

Precise alignment between the robot gripper member 30 and the selected sample tube 42 enables the sample tube 42 to be picked up by the robot 12 without interference of the robot gripper fingers 38 and 40 with other sample tubes 42 in the first sample tube rack 44.

Figure 6:
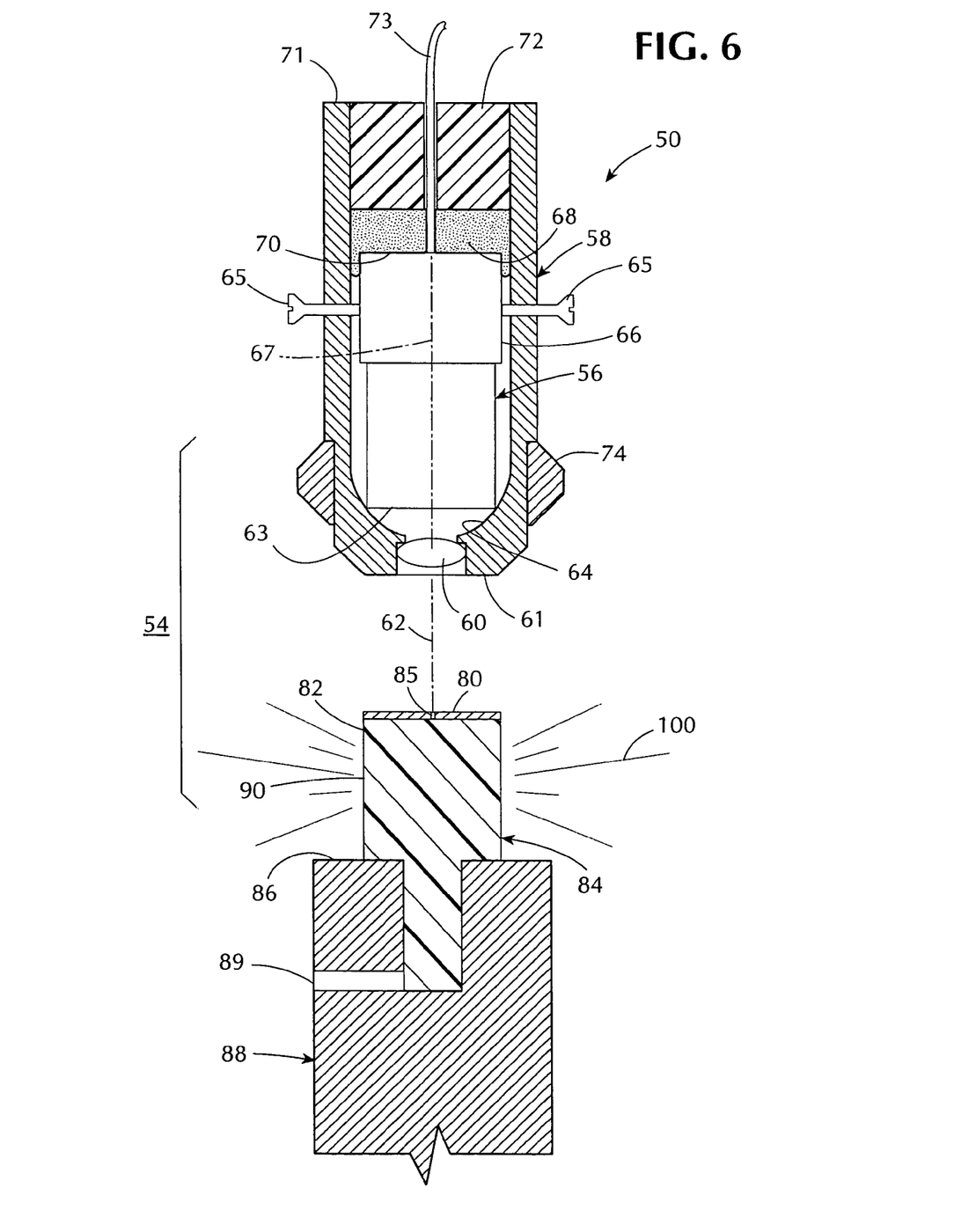
FIG. 6 is an enlarged fragmentary detail thereof, shown in section.

Predetermined robot alignment positions are established for the robot 12 using the alignment system of the present invention, one embodiment of which is generally indicated by the reference number 54 in FIG. 6.

The robot alignment system 54 includes a laser module 56 retained within a generally cylindrical laser sleeve 58. The laser module 56 is of any suitable known construction such as a model no. PLC6501AE-B laser module distributed by Lasermate Group Inc. of Pomona, Calif. A lens means 60 is centered at one end 61 of the laser sleeve 58 to permit emission of a focused laser beam 62 from the laser sleeve 58. The lens means 60 is of any suitable known construction such as a model no. J45-116 laser singlet lens distributed by Edmund Scientific Co. of Barrington, N.J. The laser module 56, the laser sleeve 58, and the lens means 60 are collectively referred to as a laser transmitter 50 (FIG. 6).

A transmission end 63 (FIG. 6) of the laser module 56 abuts an inner hemispherical surface 64 of the laser sleeve 58. Four adjustment screws 65 (FIG. 6) are provided in the laser sleeve 58 at ninety-degree intervals in the same plane. The screws 65 are adjustable against an outer surface 66 of the laser module 56 to optically align the laser module 56 with the lens means 60. Under this arrangement the focused laser beam 62 can be rendered substantially co-axial with a central axis 67 (FIG. 6) of the laser sleeve 58.

Once the laser module 56 has been optically aligned in the laser sleeve 58 with the lens means 60, a suitable known silicone potting compound 68 (FIG. 6) is provided in the laser sleeve 58 at an end portion 70 of the laser module 56. The potting compound 68 fixes the adjusted optically aligned position of the laser module 56 within the laser sleeve 58. Thus the adjustment screws 65 (FIG. 6) can be removed from the laser sleeve 58 without affecting the alignment position of the laser module 56. The adjustment screws 65 are therefore not shown in FIGS. 4 and 5.

An end 71 of the laser sleeve 58 (FIG. 6) is provided with a closure material 72 to seal the potting compound 68 and the laser module 56 within the laser sleeve 58. The closure material 72 is preferably formed from any suitable known epoxy material. A power line 73 (FIG. 6) for the laser module 56 extends through the potting compound 68 and the closure material 72 to a suitable power source (not shown).

Figure 3:
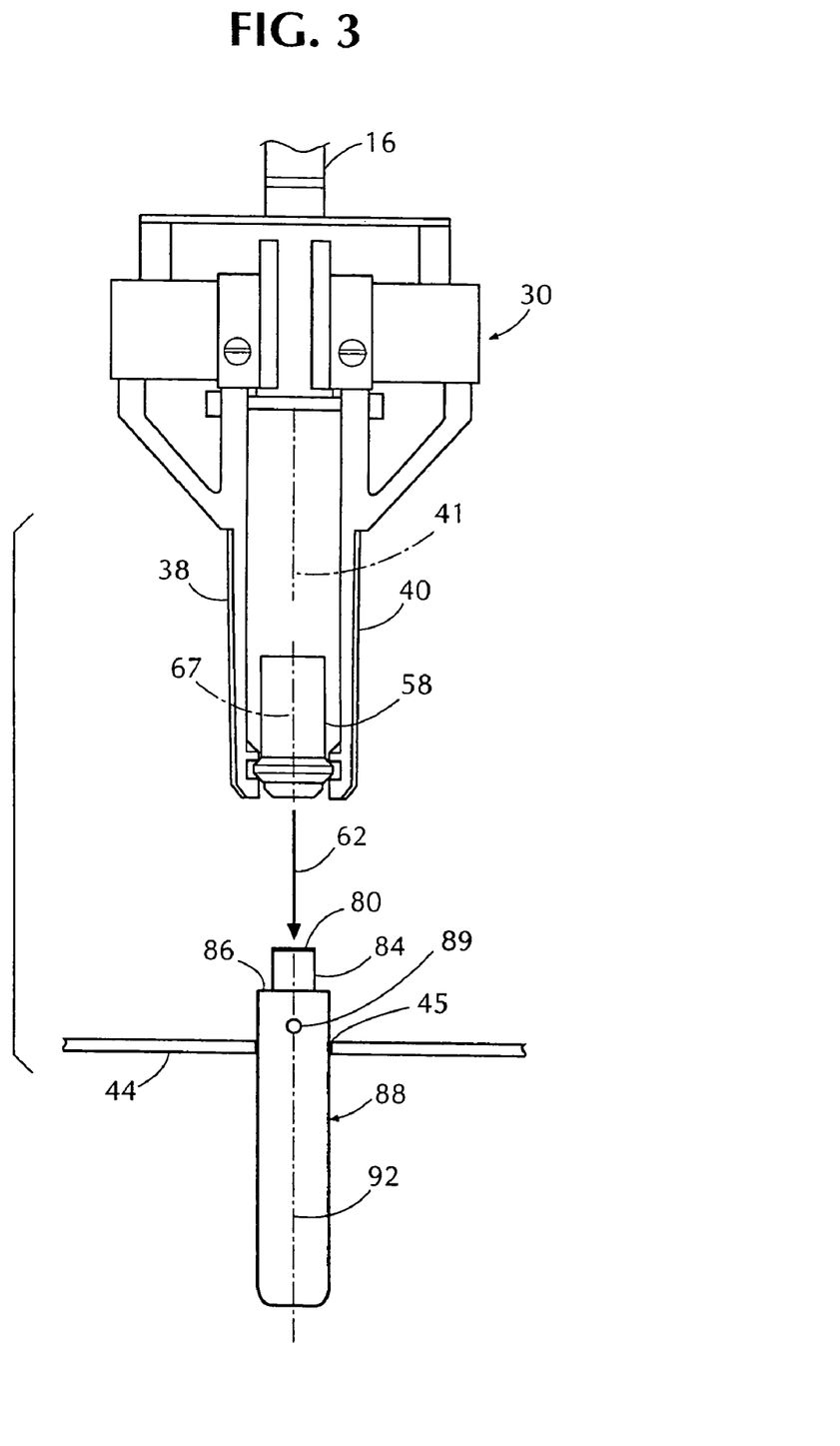
FIG. 3 is a fragmentary front view of the robot gripper member in combination with an alignment system incorporating one embodiment of the invention.

The laser sleeve 58 also includes an annular projecting collar 74 (FIG. 6) to facilitate holding of the laser sleeve 58 in gripper finger channels 75 and 76 (FIGS. 4 and 5) of the gripper member 30, such that the laser sleeve axis 67 is co-axial with the gripper finger axis 41 (FIG. 3). The projecting collar 74 can be formed integrally with the laser sleeve 58 or as a separate collar.

The robot alignment system 54 (FIG. 6) further includes a target means 80 (FIGS. 3–6) against which the focused laser beam 62 is directed. The target means 80 is preferably a stainless steel disc, such as model 1-400B-2/HS, distributed by National Aperture Inc. of Salem, N.H., adhered to an upper end 82 of a signaling means 84. The exposed stainless steel surface of the target means 80 is generally opaque to the focused laser beam 62. Thus the laser beam 62 does not normally pass directly through the stainless steel material of the target means 80.

The target means 80 is approximately 0.13 mm thick, approximately 6 mm in diameter and has a central target aperture 85 (FIG. 6) approximately 0.013 mm in diameter through which the focused laser beam 62 can pass. Although the target aperture 85 is of approximate pinhole size in diameter, it functions as a laser communication site that permits passage or transmission of the focused laser beam 62 to the signaling means 84 only when the focused laser beam 62 aligns with the target aperture 85 in the manner shown in FIGS. 5 and 6.

Figure 7:
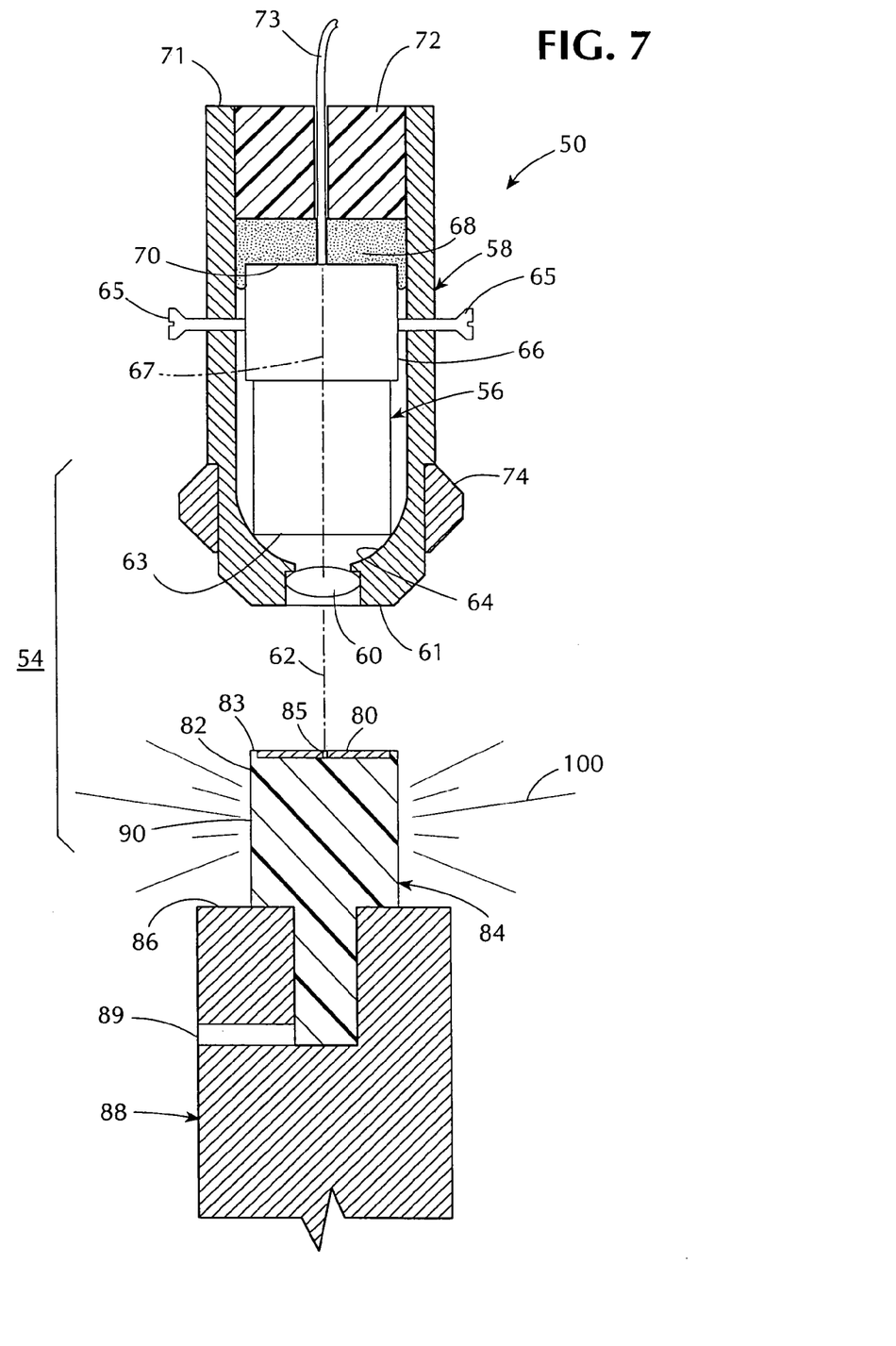
FIG. 7 is a view similar to FIG. 6 showing another embodiment of the invention; and, FIGS. 8 and 9 are views similar to FIGS. 4 and 5 showing still another embodiment of the invention.

If desired, the target means 80 can be recessed in the upper end 82 of the signaling means 84 as shown in FIG. 7. Under the arrangement of FIG. 7 any portion of the upper end 82 of the signaling means 84 that is not covered by the target means 80 can be coated with any suitable known coating 83 that is opaque to laser light.

The signaling means 84 is in the form of a plastic cylinder, preferably made of white polystyrene for example, and includes a reduced diameter section 86 recessed in an end portion 87 (FIGS. 3–6) of a structural facsimile 88 of the sample tube 42. A transverse relief opening 89 (FIG. 6) is provided in the sample tube facsimile 88 at the bottom of the reduced diameter section 86 to facilitate installation of the signaling means 84 in the end portion 87 of the sample tube facsimile 88. If desired, adhesive material (not shown) can be provided at the lower end of the reduced diameter section 86 to maintain securement of the signaling means in the sample tube facsimile 88. The signaling means 84 has an uncovered cylindrical surface portion 90.

The sample tube facsimile 88 is a solid cylindrical structure, preferably made of aluminum, having the size and shape of the sample tube 42. A central axis 92 (FIGS. 4–5) of the sample tube facsimile 88 aligns with the target aperture 85.

Referring to FIG. 3, the central axis 67 of the cylindrical laser sleeve 58 aligns with the gripper finger axis 41 when the laser sleeve 58 is held by robot gripper member 30 in the manner shown in FIG. 3. In addition the focused laser beam 62 that is emitted from the lens means 60 also aligns with the gripper finger axis 41 and the central axis 67 of the laser sleeve 58. Thus the emitted laser beam 62 is substantially co-axial with the gripper finger axis 41 (FIG. 3). Such alignment is facilitated and stabilized by engagement of the annular projecting collar 74 (FIGS. 3–5) of the laser sleeve 58 in the gripper finger channels 75 and 76 of the gripper fingers 38 and 40.

Figure 4:
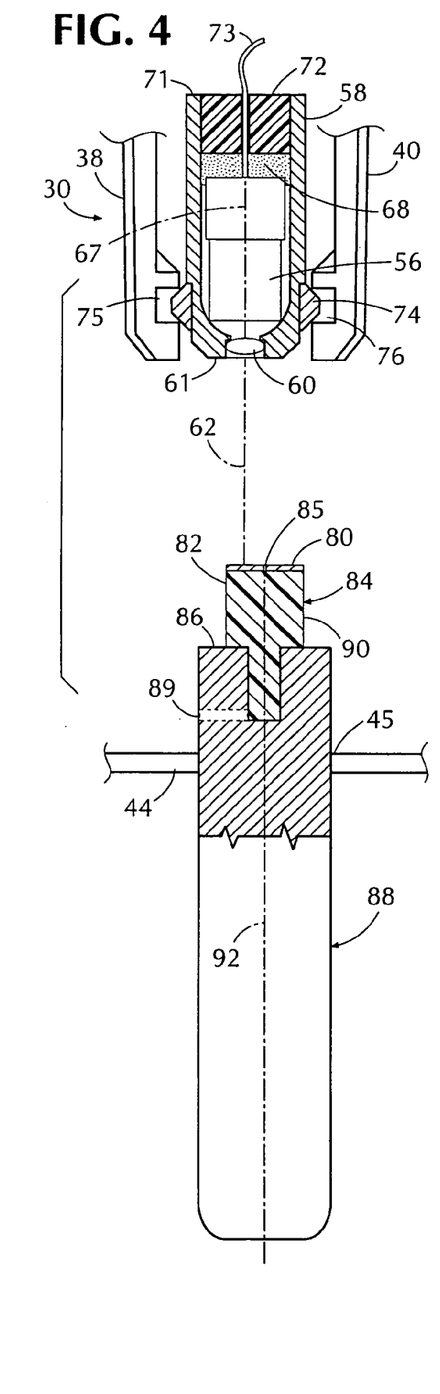
FIGS. 4 and 5 are enlarged fragmentary views thereof, partly shown in section.
Figure 5:
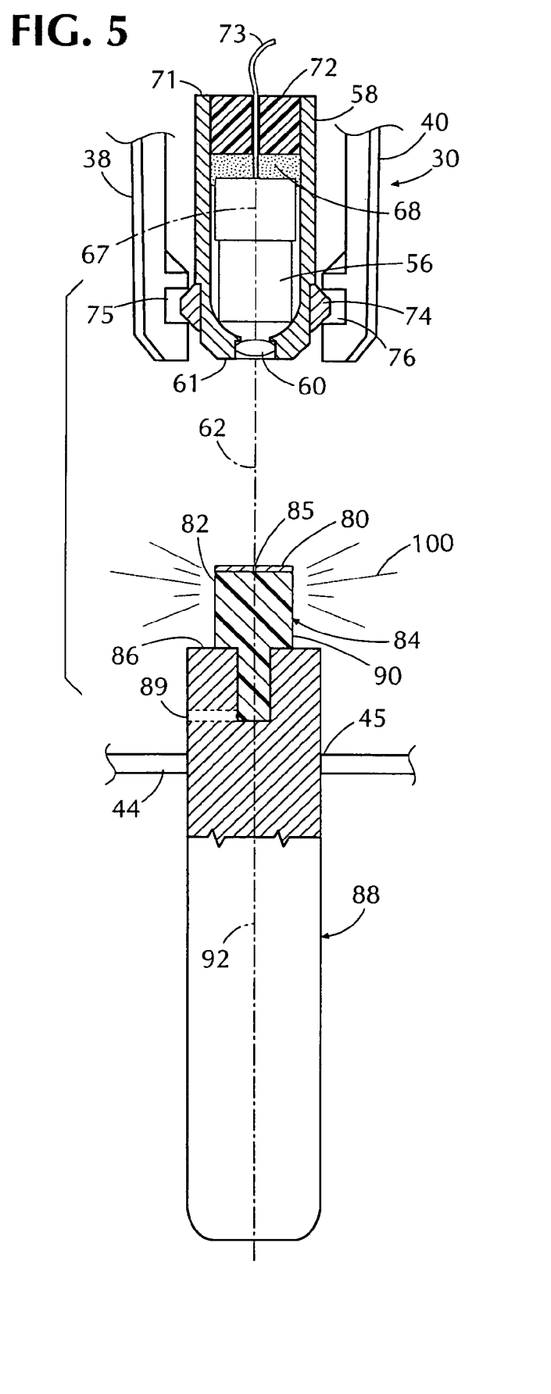

An alignment position of the robot 12 with a sample tube containment position 45 (FIG. 1) in the first sample tube rack 44 is determined by placing the sample tube facsimile 88 in the selected sample tube position 45 (FIGS. 3–5). The robot 12 is then moved to the general location of the sample tube facsimile 88 in the first sample tube rack 44, while the laser module 56, held in the robot gripper member 30, emits the focused laser beam 62 through the lens means 60. The robot gripper member 30 is moved in and around the central area of the target means 80 to enable the focused laser beam 62 to locate the target aperture 85 on the sample tube facsimile 88.

During programming of robot alignment positions for the robot control system (not shown) the robot 12 (FIGS. 1 and 2) can be motor driven or manually moved by a programming operator along the robot support rail 14. Also during such programming the laser module 56, held by the robot 12, is arranged to continuously emit the laser beam 62 from the lens means 60 when the robot gripper member 30 is in the vicinity of the sample tube facsimile 88. The robot 12 is thus moved to a position wherein the focused laser beam 62 is directed against the target means 80 of the sample tube facsimile 88 as shown in FIG. 3.

Preferably the distance between the lens means 60 and the target means 80, as shown in FIG. 3, is approximately 7 mm. When the robot 12 is positioned such that the focused laser beam 62 is transmitted through the target aperture 85 (FIGS. 5 and 6) the laser beam 62 is substantially co-axial with the central axis 92 of the sample tube facsimile 88 (FIGS. 3 and 5).

Consequently when the focused laser beam 62 passes through the target aperture 85, for transmission to the signaling means 84, the uncovered surface 90 of the signaling means 84 glows visibly, as indicated at reference number 100 in FIGS. 5 and 6. The laser induced visible glow 100 of the signaling means 84 can be easily seen by a nearby programming operator (not shown).

The laser induced visible glow 100 of the signaling means 84 signifies to the programming operator that a desired alignment between the robot gripper member 30 and the sample tube facsimile 88 has been established. In addition the laser induced visible glow 100 of the signaling means 84 alerts the programming operator take whatever steps are necessary to program the established robot alignment position in the robot control system (not shown), using known programming techniques.

The robot 12 and the laser beam 62 are thus moved to the central area of the target means 80 to "hunt" for the precise robot position that causes the focused laser beam 62 from the gripper member 30 to pass through the target aperture 85 and "light up" the signaling means 84 of the sample tube facsimile 88 in the first sample tube rack 44.

Establishment of an alignment position between the robot gripper member 30 and a selected sample tube position 45 within the sample tube rack 44 (FIGS. 1 and 5) does not involve any guesswork by a programming operator because alignment is established and signified only when the signaling means 84 is caused to visibly glow upon alignment of the focused laser beam 62 with the target aperture 85.

After the robot alignment system 54 has established an alignment position between the robot gripper member 30 and a selected sample tube containment position 45 (FIGS. 1 and 3–5) within the first sample tube rack 44, such established alignment position can be further used as a reference alignment position to determine additional robot alignment positions corresponding to other sample tube containment positions 45 in the first sample tube rack 44.

For example, because the first sample tube rack 44 is normally made to known predetermined specifications, the center-to-center distances between each sample tube containment position 45 within the sample tube rack 44 are known. Furthermore, the orientations of other sample tube containment positions 45, relative to the reference alignment position for the selected sample tube containment position 45 (FIG. 1) are known. Therefore the establishment of one robot alignment position between the robot gripper member 30 and the selected sample tube containment position 45 (FIG. 1) in the first sample tube rack 44 facilitates determination of other robot alignment positions between the robot gripper member 30 and other sample tube containment positions 45 in the first sample tube rack 44.

The programming operator can thus calculate known distances and orientations of other sample tube containment positions 45 relative to the reference alignment position of the robot gripper member 30. Such calculations can be used to determine other alignment positions of the robot gripper member 30 that correspond to other sample tube containment positions 45 in the first sample tube rack 44. The calculated alignment positions of the robot gripper member 30 can then be programmed in the robot control system. However, if desired, the alignment system 54 can be used with each sample tube containment position 45 to establish the respective robot alignment positions for all sample tube containment positions 45 in the sample tube rack 44.

The sample tube facsimile 88 can also be located in a selected sample tube containment position 48 of the second sample tube rack 46 (FIG. 1) in the sample analysis system 10. The alignment system 54 is thus usable to establish alignment between the robot gripper member 30 and selected sample tube containment positions 48 in the second sample tube rack 46. The robot arm 16 is moved with the laser transmitter 56 to the sample tube rack 46 while the laser transmitter 56 continues to emit the focused laser beam 62.

Therefore, in a manner similar to that previously described for the first sample tube rack 44, a robot alignment position for a selected sample tube containment position 48 in the second sample tube rack 46 can be established and signified. The robot alignment position is established when the laser beam 62 aligns with the target aperture 85 of the sample tube facsimile 88 located in the selected sample tube containment position 48 of the second sample tube rack 46. The established robot alignment position is signified when the laser beam 62 causes the signaling means 84 to visibly glow in a manner similar to that previously described for the first sample tube rack 44.

Once a robot alignment position has been established for the sample tube facsimile 88 in the second sample tube rack 46, that robot alignment position can also be used as a reference position to determine further robot alignment positions between the robot gripper member 30 and other sample tube containment positions 48 in the second sample tube rack 46. The further robot alignment positions can be determined in a manner similar to that previously described for the first sample tube rack 44, by calculation of known center-to-center distances and orientations of other sample tube containment positions 48 within the second sample tube rack 46.

In this manner the robot control system can be programmed to automatically move the robot 12 to the robot alignment positions that correspond to sample tube positions 45 and 48 in the first and second sample tube racks 44 and 46.

The robot 12, when moved to a selected robot alignment position, can then automatically perform desired processing operations on the sample tube 42. Such processing operations may include automatic descent of the robot gripper member 30 toward the first sample tube rack 44 to grip and pick up the selected sample tube 42 from the sample tube rack 44, elevation of the robot gripper member 30 with the sample tube 42, and movement of the robot gripper member 30 with the sample tube 42 to the second sample tube rack 46 for release of the sample tube 42 in a predetermined sample tube containment position 48 within the second sample tube rack 46.

All sample tube pick up positions and sample tube release positions correspond to robot alignment positions previously established using the robot alignment system 54. The robot 12 can then sequentially remove sample tubes 42 from the first sample tube rack 44 for movement to and release in the second sample tube rack 46 and so on.

Figure 8:
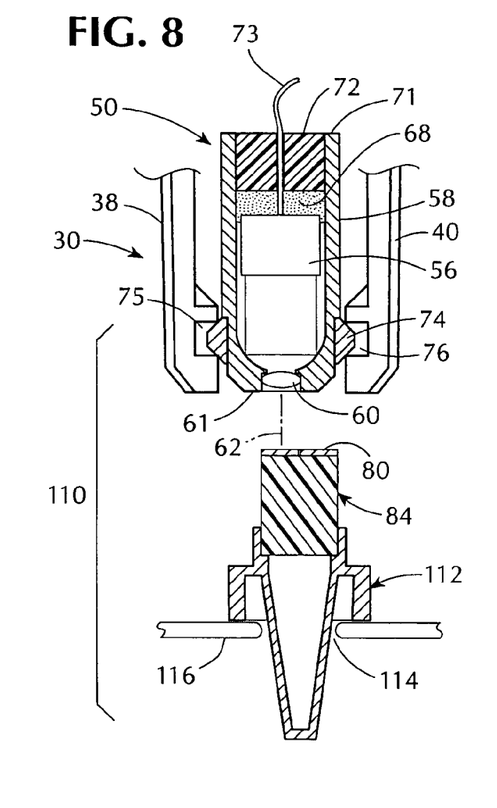

Another embodiment of the alignment system is generally indicated by the reference number 110 in FIG. 8. The alignment system 110 cooperates with the robot gripper member 30.

The robot alignment system 110 includes the laser transmitter 50, the target means 80 and the signaling means 84. The signaling means 84 is supported in a feeder cup facsimile 112 that is made to the size and shape of a known feeder cup used in a sample analysis system. The feeder cup facsimile is located in a feeder cup containment space 114 of a known sample rack 116 used in a sample analysis system of the type shown in FIG. 1 and detailed in U.S. Pat. No. 6,293,750.

Figure 9:
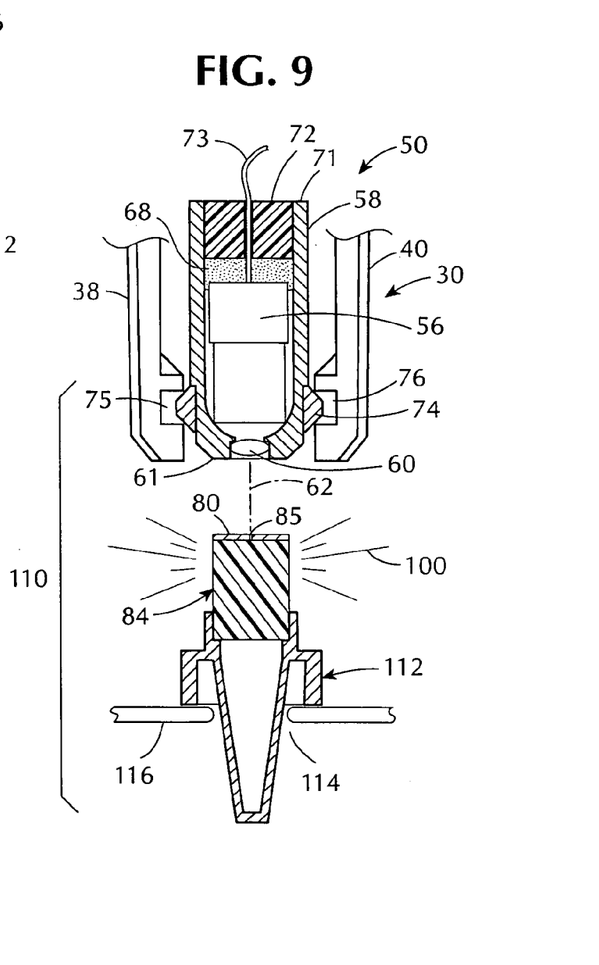

Robot alignment positions are established between the robot 12 and the feeder cup containment space 114 of the sample rack 116 in a manner similar to that previously described for the robot alignment system 54. Thus once a robot alignment position is established in the manner shown in FIG. 9, other robot alignment positions can be established for other containment spaces 114 in the sample rack 116 in a manner similar to that previously described for the alignment system 54.

After the respective robot alignment positions have been established for all containment spaces 114 in the sample rack 116 the robot 12 can be programmed to automatically transfer feeder cups (not shown) from the sample rack 116 to delivery destinations within the sample analysis system. Therefore robot alignment positions are also established using the alignment system 110 for all delivery destinations of respective feeder cups (not shown) where the pick up and delivery functions are performed by the robot 12.

In view of the above, it will be seen that the several objects of the invention are achieved and other advantageous results obtained.

As various changes can be made in the above constructions and method without departing from the scope of the invention, it is intended that all subject matter contained in the above description or shown in the accompanying drawings shall be interpreted as illustrative and not in a limiting sense.

What is claimed is:

1. A method of establishing a predetermined alignment position between an operating member and an article before processing of the article by the operating member comprising,
   a) supporting a laser transmitter on one of the operating member and the article, and providing the laser transmitter with means for emitting a focused laser beam,
   b) supporting a target means for the focused laser beam from the laser transmitter, on the other of the operating member and the article,
   c) providing a signaling means in cooperation with the target means to produce a detectable signal when the operating member and the article are aligned,
   d) providing a laser beam communication site at a selected location on the target means for receiving the focused laser beam and transmitting the focused laser beam to the signaling means to enable the signaling means to produce the detectable signal when the focused laser beam is received at the signaling means, and
   e) moving one of the operating member and the article to a position wherein the focused laser beam from the laser transmitter is received at the laser beam communication site for transmission of the focused laser beam to the signaling means to enable the signaling means to produce the detectable signal, whereby the production of the detectable signal by the signaling means, in response to reception of the focused laser beam at the laser beam communication site, signifies the establishment of the alignment position between the operating member and the article that is processed by the operating member.

2. The method as claimed in claim 1 including moving the operating member with respect to the article to the position wherein the focused laser beam is received at the laser beam communication site.

3. The method as claimed in claim 1 including supporting the laser transmitter on the operating member, and supporting the target means and the signaling means on the article that is processed by the operating member.

4. The method as claimed in claim 3 including forming the target means of a material that is opaque to the focused laser beam and locating the target means on the signaling means.

5. The method of claim 4 including providing an opening of approximate pinhole size in the target means material, at the selected location, to constitute the laser beam communication site so as to enable the focused laser beam to pass through the target means only at the opening of approximate pinhole size at the laser beam communication site, to enable the transmitted laser beam to cause the signaling means to produce the detectable signal.

6. The method as claimed in claim 1 including providing the laser beam communication site within an area of approximate pinhole size at the selected location on the target means for receiving the focused laser beam from the laser transmitter.

7. The method as claimed in claim 6 including forming the signaling means of a translucent material that glows when the transmitted laser beam is received by the signaling means, and providing the signaling means with an uncovered surface that glows visibly when the transmitted laser beam is received by the signaling means through the opening of approximate pinhole size in the target means, whereby the visible glow of the signaling means establishes the predetermined alignment position between the operating member and the article that is processed by the operating member.

8. An alignment kit for establishing an alignment position between a movable operating member and an article that can be processed by the movable operating member comprising,
   a) a laser transmitter having means for emitting a focused laser beam, the laser transmitter being of a first predetermined size and shape to permit the laser transmitter to be carried by one of the movable operating member and the article,
   b) target means against which the focused laser beam is directed, the target means being of a second predetermined size and shape to permit the target means to be carried by the other of the movable operating member and the article, and
   c) signaling means cooperable with the target means for producing a detectable signal when the focused laser beam is received by the signaling means, whereby the production of the detectable signal by the signaling means in response to reception of the focused laser beam signifies establishment of the predetermined alignment position between the movable operating member and the article that is processed by the movable operating member.

9. The alignment kit as claimed in claim 8, wherein the target means is formed of a material that is opaque to the focused laser beam and includes a communication site formed as an aperture of approximate pinhole size in the opaque material to permit passage of the focused laser beam through the target means only at the aperture of approximate pinhole size for transmission to the signaling means to enable the signaling means to produce the detectable signal that signifies establishment of the predetermined alignment position between the movable robot member and the article that is processed by the movable robot member.

10. A method of establishing a predetermined alignment position between a movable robot member and an article that is processed by the movable robot member comprising,
    a) supporting a laser transmitter on one of the robot member and the article, and providing the laser transmitter that emits a focused laser beam,
    b) supporting a target for the focused laser beam from the laser transmitter, on the other of the robot member and the article,
    c) providing a signal producer in cooperation with the target to produce a detectable signal when the operating member and the article are aligned,
    d) providing a laser beam communication site at a selected location on the target for receiving the focused laser beam and transmitting the focused laser beam to the signal producer to enable the signal producer to produce the detectable signal when the focused laser beam is received at the signal producer, and
    e) moving one of the robot member and the article to a position wherein the focused laser beam from the laser transmitter is received at the laser beam communication site for transmission of the focused laser beam to the signal producer to enable the signal producer to produce the detectable signal, whereby the production of the detectable signal by the signal producer, in response to reception of the focused laser beam at the laser beam communication site, signifies the establishment of the alignment position between the robot member and the article that is processed by the robot member.

11. The method as claimed in claim 10 including supporting the laser transmitter on the operating member, forming the target of a material that is opaque to the focused laser beam and locating the target on the signal producer, and supporting the target and the signal producer on the article that is processed by the operating member.

12. The method of claim 11 including providing an opening of approximate pinhole size in the target material, at the selected location, to constitute the laser beam communication site so as to enable the focused laser beam to pass through the target only at the opening of approximate pinhole size at the laser beam communication site, to enable the transmitted laser beam to cause the signal producer to produce the detectable signal.

13. A robot alignment system for establishing a predetermined alignment position between a movable robot member and an article that is processed by the movable robot member comprising,
   a) a laser transmitter having means for emitting a focused laser beam, the laser transmitter being of a first predetermined size and shape to permit the laser transmitter to be supported by one of the movable robot member and the article,
   b) target means against which the focused laser beam is directed, the target means being of a second predetermined size and shape to permit the target means to be supported by the other of the movable robot member and the article that is processed by the movable robot member, and
   c) signaling means cooperable with the target means for producing a detectable signal when the focused laser beam is received at a predetermined location on the target means, whereby the production of the detectable signal by the signaling means signifies establishment of the predetermined alignment position between the movable robot member and the article that is processed by the movable robot member.

14. The robot alignment system as claimed in claim 13, wherein the laser transmitter is sized and shaped to be supported by the movable robot member, and the target means is sized and shaped to be supported by the article that is processed by the movable robot member.

15. The robot alignment system as claimed in claim 14, wherein the target means is combined with a structural facsimile of the article processed by the movable robot member.

16. The robot alignment system as claimed in claim 14, wherein the signaling means is combined with a structural facsimile of the article processed by the movable robot member.

17. The robot alignment system as claimed in claim 14 wherein the signaling means and the target means are combined with a structural facsimile of the article processed by the movable robot member.

18. The robot alignment system as claimed in claim 13, wherein the target means includes a communication area of approximate pinhole size which receives and transmits the focused laser beam to the signaling means to enable the signaling means to produce the detectable signal that signifies establishment of the predetermined alignment position between the movable robot member and the article that is processed by the movable robot member.

19. The robot alignment system as claimed in claim 13, wherein the target means is formed of a material that is opaque to the focused laser beam and includes a communication site formed as an aperture of approximate pinhole size in the opaque material to permit passage of the focused laser beam through the target means only at the aperture of approximate pinhole size for transmission to the signaling means to enable the signaling means to produce the detectable signal that signifies establishment of the predetermined alignment position between the movable robot member and the article that is processed by the movable robot member.

20. The robot alignment system as claimed in claim 19, wherein the signaling means is formed of a selected translucent material that glows when the focused laser beam enters the translucent material, through the aperture of approximate pinhole size in the target means, one portion of the translucent material being an uncovered surface area that visibly glows when the focused laser beam passes through the aperture of approximate pinhole size in the target means for entry into the translucent material, whereby the visible glow of the translucent material signifies establishment of the predetermined alignment position between the movable robot member and the article that is processed by the movable robot member.

21. The robot alignment system as claimed in claim 20, wherein the target means is a metallic strip bonded to said translucent material such that the focused laser beam can only pass through the aperture of approximate pinhole size that is formed in the metallic strip.

* * * * *